United States Patent [19]

Renger

[11] Patent Number: 5,488,553
[45] Date of Patent: Jan. 30, 1996

[54] POWER CONVERTER APPARATUS FOR DEFIBRILLATING CARDIAC PACEMAKER

[75] Inventor: Herman L. Renger, Calabasas, Calif.

[73] Assignee: Pacesetter, Inc., Sylmar, Calif.

[21] Appl. No.: 168,735

[22] Filed: Dec. 15, 1993

[51] Int. Cl.$^6$ .................................................. A61N 1/00
[52] U.S. Cl. .................................... 363/21; 607/5; 607/7
[58] Field of Search ........................ 307/66, 150; 607/7; 363/20–21, 97, 131, 24–26, 39–41, 132–134; 320/1; 315/241 P

[56] References Cited

U.S. PATENT DOCUMENTS

| | | | |
|---|---|---|---|
| 5,285,779 | 2/1994 | Cameron et al. | 607/5 |
| 5,313,881 | 5/1994 | Balakrishnan | 363/147 |
| 5,381,327 | 1/1995 | Yan | 363/24 |

Primary Examiner—Peter S. Wong
Assistant Examiner—Adnya Krishnan
Attorney, Agent, or Firm—Malcolm J. Romano

[57] ABSTRACT

A power converter apparatus adapted for use in a defibrillating cardiac pacemaker, to selectively provide a prescribed high voltage useful in treating a cardiac fibrillation. A pulse generator-cyclically applies a relatively low battery voltage $V_s$ to a step-up transformer, to controllably charge a high-voltage capacitor. The time durations of the cyclic applications of the battery voltage $V_s$ are controlled by digital feedback of several parameters, including peak transformer current, average transformer current, battery voltage $V_s$, and the voltage on the high-voltage capacitor. If any of the measured parameters is determined to be outside a predetermined limit, the pulsing of the transformer is incrementally modified. A smooth, efficient charging of the high-voltage capacitor thereby is provided.

20 Claims, 2 Drawing Sheets

POWER CONVERTER APPARATUS FOR DEFIBRILLATING CARDIAC PACEMAKER

BACKGROUND OF THE INVENTION

This invention relates generally to defibrillating cardiac pacemakers and, more particularly, to power converter apparatus of such pacemakers for rapidly providing a high dc voltage based on a relatively low battery voltage.

Implantable cardiac pacemakers of this kind have the capability of detecting cardiac fibrillations and treating such detected fibrillations by applying to the heart a predetermined high voltage. Such pacemakers do not maintain the predetermined high voltage continuously, but rather produce the voltage only when the need for defibrillation arises. When that need arises, the high voltage must be provided as rapidly and as efficiently as possible, without excessively drawing down the voltage of the pacemaker's battery.

Implantable defibrillating cardiac pacemakers of this kind typically charge a high-voltage capacitor to a voltage of about 750 volts, storing about 40 joules of energy. Typically, the pacemaker's battery voltage is applied periodically to the primary winding of a step-up transformer, to cause current pulses to be coupled from the transformer's secondary winding through a rectifier to the high-voltage capacitor. Such transformers typically have been driven into saturation, which leads to inefficiency and wasting of the limited battery power available. In some instances, this circuitry can draw down the battery voltage to a point where other circuits in the pacemaker are adversely affected. In addition, the application of pulsed power to the transformer's input winding can create electromagnetic interference that interferes with such other circuits.

The implantable defibrillating cardiac pacemakers of the kind described briefly above have functioned generally satisfactorily in providing the high voltage needed to terminate detected fibrillations. However, such pacemakers are not believed to have provided that high voltage as rapidly and as efficiently as is possible. The need remains for a power converter apparatus suitable for use in an implantable defibrillating cardiac pacemaker, where the apparatus provides the required high voltage with reduced time delay and with reduced wastage of limited battery power. The present invention fulfills this need.

SUMMARY OF THE INVENTION

The present invention is embodied in a power converter apparatus adapted for use in a defibrillating cardiac pacemaker, which selectively charges a capacitor to a predetermined high voltage in a minimum time, while wasting only minimal power from a low-voltage battery source. The apparatus includes a transformer having a primary winding and a secondary winding, a rectifier connected to the secondary winding and having a capacitor for carrying the predetermined high voltage, and a pulse-width modulator for intermittently applying the low-voltage battery power to the transformer's primary winding, whereupon an electrical current is induced intermittently in the transformer's secondary winding, to charge the capacitor. Feedback control means measures one or more predetermined parameters of signals present in the transformer and/or rectifier, to produce one or more binary feedback signals that are coupled to the pulse-width modulator. This controllably adjusts the successive time durations of the intermittent applications of the battery power to the transformer's primary winding, such that the capacitor is charged to the predetermined high voltage in a minimum time, with minimum adverse effect on the low-voltage battery source.

In a more detailed feature of the invention, the pulse-width modulator applies the battery power to the transformer's primary winding cyclically, at regular intervals of time, and the feedback control means includes a comparator, operable during each cycle of the first pulse-width modulator, for comparing a predetermined parameter of a signal present in the transformer with a predetermined threshold, to generate a corresponding binary control signal. Further, the pulse-width modulator includes an up/down counter along with means for cyclically generating a sequence of pulses, each pulse having a time duration selected according to the current count registered in the up/down counter. The pulse-width modulator further includes means operable during each cycle for incrementing or decrementing the count registered in the up/down counter according to the binary control signal generated by the comparator. The duration of each application of the battery power to the transformer's primary winding thereby is controllably adjusted so as to optimize the charging of the capacitor.

In another more detailed feature of the invention, as many as four separate parameters of signals present in the transformer and the rectifier are measured and used to control the pulse-width modulator. Specifically, the parameters that are measured can include the voltage present on the high-voltage capacitor, the peak current conducted through the transformer's primary winding, the total charge conducted during each cycle through the transformer's primary winding, and the voltage of the battery. The measurements of these parameters are compared with predetermined thresholds, to produce up to four binary feedback signals. These four binary feedback signals are ORed in an OR gate, to produce a single combined feedback signal that is coupled to the pulse-width modulator.

In addition, the binary feedback signals produced according to the peak current conducted through the transformer's primary winding and the total charge conducted through the primary winding during each cycle can be ORed in an OR gate, to produce a second combined feedback signal. This signal is coupled to the pulse-width modulator to immediately terminate the current application of battery power to the transformer's primary winding.

The means for measuring the high-voltage capacitor voltage can include a second pulse-width modulator for intermittently generating a pulse whose duration corresponds to the measured voltage. An optocoupler can couple this pulse to a comparator for measuring the pulse duration and comparing that measurement with a predetermined threshold. This effectively provides dc isolation for the high-voltage capacitor.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENT

Figure 1:
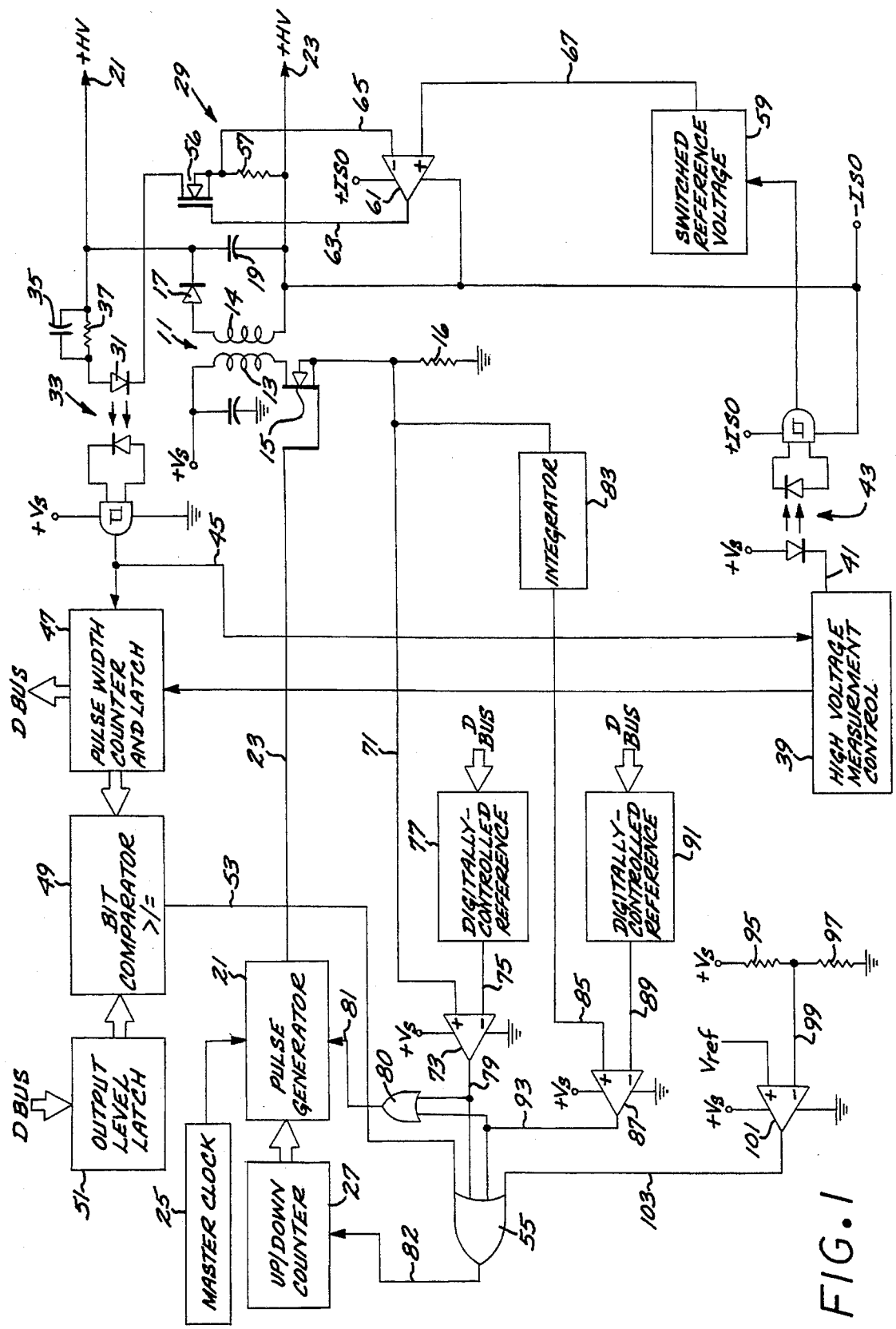
FIG. 1 is a simplified block diagram of a power converter apparatus in accordance with the invention.

With reference now to the drawings, and particularly to FIG. 1, there is shown a power converter apparatus adapted for use in an implantable defibrillating cardiac pacemaker, to selectively provide a predetermined high voltage when a cardiac fibrillation has been detected. The apparatus produces the high-voltage output based on a low voltage $V_s$ provided by a pacemaker battery (not shown). Until the pacemaker detects a cardiac fibrillation, the power converter apparatus is idle and its output voltage is 0 volts. When a fibrillation is detected, however, the power converter apparatus immediately begins operating to attain the required high-voltage output as rapidly as possible, with minimal wastage of power from the low-voltage battery source and with limited adverse effect on the battery's voltage $V_s$. The required high voltage typically is on the order of 750 volts, and typically about 40 joules of energy must be available for rapid delivery.

The power converter apparatus of FIG. 1 includes a transformer 11 having a primary winding 13 and a secondary winding 14. One terminal of the primary winding is connected directly to the low-voltage battery, and the other terminal of the primary winding is connected through a field-effect transistor 15 and a current-sensing series resistor 16 to ground. The secondary winding is connected to a rectifier that includes a diode 17 and a high-voltage capacitor 19. The two terminals of the capacitor are connected directly to two high-voltage output terminals 21 and 23, which in turn are connected to the pacemaker's high-voltage switching circuit (not shown), for selective application to defibrillation electrodes.

Figure 2:
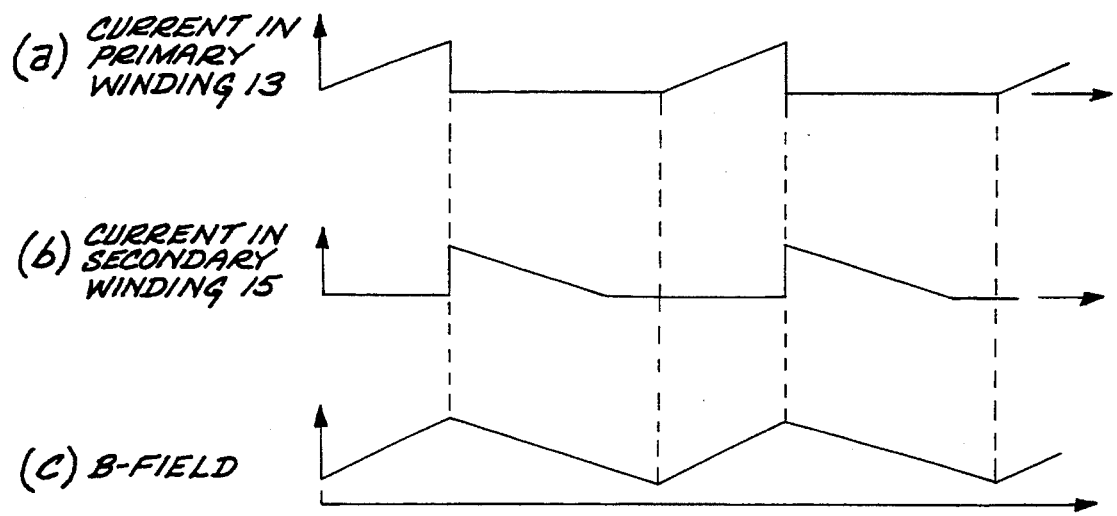
FIGS. 2(a), (b) and (c) are timing diagrams of signals present in the transformer of the power converter apparatus of FIG. 1.
Figure 3:
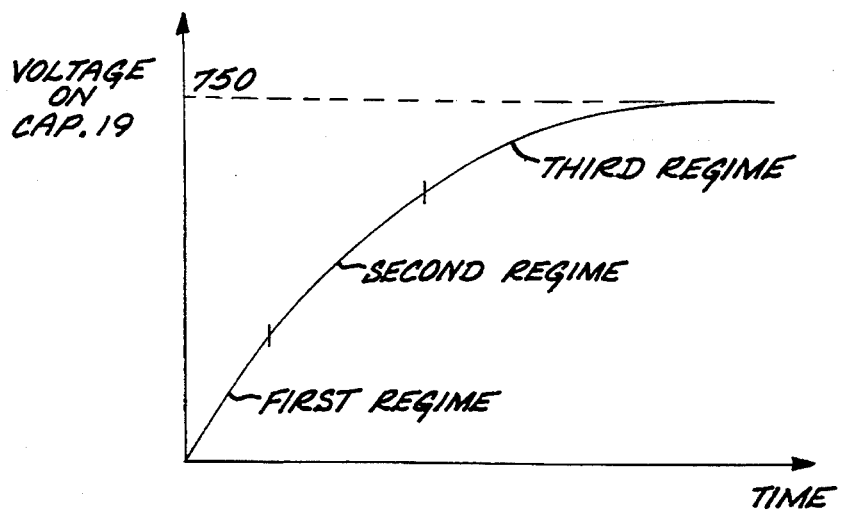
FIG. 3 is a graph depicting the rising voltage on the high-voltage capacitor during operation of the power converter apparatus of FIG. 1.

The transistor 15 is periodically switched ON, to apply the voltage $V_s$ across the primary winding 13 of the transformer 11. The resulting electrical current ramps upwardly for as long as the transistor remains switched ON, which causes the B-field in the transformer likewise to ramp upwardly. The primary winding current and the B-field are depicted in FIGS. 2(a) and 2(c), respectively.

When the transistor 15 is switched OFF, the B-field in the transformer 11 collapses and electrical current is induced to flow through the secondary winding 14. This current flows through the diode 17 to charge the high-voltage capacitor 19. FIG. 2(b) depicts this secondary winding current.

Because of the urgency of treating the detected fibrillation with as little time delay as possible, it is desirable to charge the high-voltage capacitor 19 as rapidly as possible. On the other hand, because of the limited battery power available and because of the critical need for other pacemaker circuits to continue operating effectively, it is desirable to waste as little battery power as possible and not to unduly draw down the battery voltage $V_s$. The power converter apparatus therefore monitors several parameters of signals present in the transformer 11, as well as the high voltage output itself, and provides digital feedback for efficiently controlling the charging operation.

In particular, the monitored parameters include (1) the voltage present on the high-voltage capacitor 19, (2) the peak current conducted through the primary winding 13 of the transformer 11, (3) the average current conducted through the primary winding during each cycle, and (4) the instantaneous battery voltage $V_s$. If any of the measured parameters is determined to be beyond a predetermined threshold during a particular cycle of the pulsing of the transformer, then the duration of the pulse applied to the transistor 15 during the next cycle of operation is incrementally reduced. On the other hand, if none of the measured parameters is determined to be beyond its corresponding threshold, then the duration of the pulse applied to the transistor during the next cycle is incrementally increased. In addition, if either of the measured parameters (2) or (3) is determined to be beyond its corresponding threshold during a particular cycle, then the conduction of current through the primary winding 13 is immediately terminated. This leads to an efficient charging of the high-voltage capacitor 19.

More particularly, the power converter apparatus includes a pulse generator 21 for supplying periodic control pulses on line 23 to the gate terminal of the transistor 15. A master clock 25 drives the pulse generator so as to initiate each such pulse. The pulse generator controllably adjusts the duration of each such control pulse according to a digital count stored in an up/down counter 27. This count is incremented upwardly or downwardly, as previously mentioned, according to the outcome of the comparisons of the identified signal parameters with their associated thresholds. A 4-bit counter is considered suitable, resulting in 16 different pulse durations. The counter limits itself so as not to count beyond its maximum and minimum counts.

The cycle frequency for the pulse generator preferably is about 500 kilohertz. This frequency minimizes interference with other circuitry in the pacemaker, including circuitry for data communications, which typically occurs at bit rates at or below about 32 kilobits per second, and circuitry for cardiac sensing, which involves frequencies below about 80 hertz.

A measurement of the voltage present on the high-voltage capacitor 19, which is supplied to the high-voltage output terminals 21 and 23, is provided by circuitry that is located generally on the top and right side of FIG. 1. This circuitry includes a constant-current source generally indicated by the reference numeral 29, which is arranged to conduct current through an LED portion 31 of an optoisolator 33 and a parallel-connected capacitor 35 and resistor 37, all arranged in parallel with the high-voltage capacitor 19. Operation of the constant-current source 29 is initiated by a high-voltage measurement control circuit 39.

When it is desired to measure the voltage present on the high-voltage capacitor 19, the high-voltage measurement control circuit 39 outputs a pulse on line 41, which is transmitted via an optoisolator 43 to switch ON the constant-current source 29. The capacitor 35 then charges uniformly until it reaches a voltage substantially equal to the voltage on the high-voltage capacitor 19. When it reaches this level, current flow ceases and the control circuit 39 automatically switches OFF the constant-current source.

While the capacitor 35 is charging, the LED 31 continuously emits light. The emitted light is detected by the detector portion of the optoisolator 33, which produces an electrical pulse of corresponding duration on line 45. A pulse-width counter and latch 47 measures the duration of this pulse to provide a corresponding digital count, and a bit comparator 49 compares this count with a selected threshold count received from an output level latch 51. This threshold count is a measure of the desired, or target, voltage for the high-voltage capacitor 19. If the bit comparator determines that the measured count is equal to or greater than the target count, it outputs a high logic level on line 53 for coupling through an OR gate 55 to the up/down counter 27, whereupon the counter is incrementally decremented. Consequently, the pulse generator 21 is caused to incrementally reduce the duration of the pulse it produces during the next succeeding cycle. This sequentially diminishes to zero the charging process. The count provided by the pulse-width counter and latch 47 preferably is represented by an 8-bit word, which provides a resolution of about 3 volts.

The digital count provided by the pulse-width counter and latch 47 also can be made available to other circuitry (not shown) in the pacemaker. This can be used, for example, to indicate the amount of charge on the high-voltage capacitor 19 after a defibrillation procedure has been effected.

The pulse from the optoisolator 33 also is supplied on line 45 to the high-voltage measurement control circuit 39. When the pulse ends, indicating that the capacitor 35 has charged to a voltage substantially equal to the voltage on the high-voltage capacitor 19, the high-voltage measurement control circuit 39 responds by terminating its output pulse on line 41. This switches off the constant-current source 29. The capacitor 35 then discharges through the shunt resistor 37. The resistor's resistance value is selected so that the capacitor 35 is substantially fully discharged within about 100 milliseconds, after which time the high-voltage measurement control circuit 39 again can be caused to initiate a voltage measurement sequence. This 100-millisecond time delay is selected as a trade off between a desire to measure the voltage on the high-voltage capacitor 19 as frequently as possible and a desire to minimize energy dissipation in the resistor 37.

The constant-current source 29 includes a field-effect transistor 56 and a current-limiting resistor 57 arranged in series with the LED portion 31 of the optoisolator 33 and with the parallel-connected capacitor 35 and resistor 37. A reference voltage source 59 and an operational amplifier 61 control the transistor's operation. In particular, the operational amplifier's output terminal is connected via line 63 to the transistor's gate terminal, while the operational amplifier's negative input terminal is connected via line 65 to the transistor's source terminal and the operational amplifier's positive input terminal is connected via line 67 to the reference voltage source 59.

When the reference voltage source 59 is enabled by the high-voltage measurement control circuit 39 via the optoisolator 43, it provides a predetermined reference voltage on line 67 to the operational amplifier. The operational amplifier thereupon outputs an appropriate signal on line 63 to the gate terminal of the transistor 56, to controllably bias the transistor ON so as to conduct sufficient current to create a voltage drop across the resistor 57 equal to the reference voltage. This constant current charges the capacitor 35 and causes the LED portion 31 of the optoisolator 33 to emit light. It will be appreciated that other known constant-current sources alternatively can be used.

It thus will be appreciated that the high-voltage portion of the power converter apparatus is dc-isolated from the low-voltage circuitry. The only interface between the two circuit portions is provided by the transformer 11 and by the two optoisolators 33 and 43. This isolation is important in ensuring that large electrical currents are not conducted along the pacemaker's sensing/pacing leads. Electrical power for the optoisolator 43, the reference voltage source 59, and the operational amplifier 61 is provided by a separate regulated voltage source (not shown) that itself is isolated by a transformer from the remaining the low-voltage circuitry of FIG. 1.

As previously mentioned, the power converter apparatus also measures several parameters of signals present in the transformer 11, for use in controlling the pulse generator 21 that controllably switches the transistor 15. In particular, the apparatus measures (1) the instantaneous electrical current conducted through the transformer's primary winding 13, (2) the average current conducted through the primary winding during each cycle, and (3) the battery voltage $V_s$.

The instantaneous current conducted through the transformer's primary winding 13 is measured by the current-sensing resistor 16, which preferably has a resistance of about 0.01 ohms. The node between this resistor and the transistor 15 is connected via line 71 to a comparator 73, which compares the node voltage with a threshold supplied on line 75 from a digitally-controlled reference 77. If the threshold is exceeded at any time during an operating cycle, then it is determined that the peak current during that cycle is too high and the comparator 73 therefore outputs a binary signal on line 79. This binary signal is coupled through an OR gate 80 and, in turn, on line 81 to the pulse generator 21, to immediately terminate the pulse being supplied to the transistor 15. This terminates further conduction of current through the primary winding 13 of the transformer 11 during the current operating cycle.

The binary signal on line 79 also is coupled through the OR gate 55 and, in turn, on line 82 to the up/down counter 27, to decrement the count currently stored in the counter. The duration of the pulse that is output by the pulse generator 21 during the next operating cycle therefore will be incrementally reduced. This feedback control ensures that the instantaneous current is never so high as to cause the transformer 11 to operate inefficiently.

The average electrical current conducted through the primary winding 13 of the transformer 11 is measured by an integrator 83 that is connected via line 71 to the node between the transistor 15 and the current-sensing resistor 16. This integrator is reset at the beginning of each operating cycle. The integrator produces a voltage representative of the total charge conducted through the primary winding during each cycle, which corresponds to the average current conducted during that cycle. This voltage measurement is conducted on line 85 to a comparator 87, which compares the voltage with a threshold supplied on line 89 from a digitally-controlled reference 91. If the threshold is exceeded, it is determined that the average current is too high and the comparator outputs an appropriate binary signal on line 93. This binary signal is coupled through the OR gate 80 and, in turn, on line 81 to the pulse generator 21, to immediately terminate the pulse being supplied to the transistor 15. This terminates further conduction of current through the primary winding 13 of the transformer 11 during the current operating cycle.

The binary signal on line 93 also is coupled through the OR gate 55 and, in turn, on line 82 to the up/down counter 27, to decrement the count currently stored in the counter. Consequently, during the next cycle of operation, the pulse generator 21 is caused to output a pulse having an incrementally-reduced time duration. This ensures that the average current conducted through the primary winding is never so high as to cause the transformer 11 to operate inefficiently.

Finally, a measure of the battery voltage $V_s$ is provided by a resistor divider that includes resistors 95 and 97. The two resistors are connected in series between the battery and ground, and the node between the two resistors is connected via line 99 to a comparator 101, for comparison with a predetermined threshold. If the voltage measurement is ever sensed to be less than the threshold, it is determined that the apparatus is unduly drawing down the battery voltage. The comparator then supplies an appropriate signal on line 103 to the OR gate 55 and, in turn, on line 82 to the up/down counter 27, to decrement the count currently stored in the counter. Consequently, during the next operating cycle, the pulse generator 21 will be caused to provide a pulse having an incrementally reduced time duration. This ensures that the battery voltage $V_s$ is never drawn down excessively, to a point where other critical circuits in the pacemaker are adversely affected.

When the power converter apparatus is called upon to provide a high-voltage output, its charging sequence ordinarily will cause it to pass through several operating regimes. Initially, the apparatus will be peak-current limited. In other words, the durations of the pulses cyclically applied by the pulse generator 21 to the transistor 15 and transformer 11 will be controlled principally by the peak current conducted through the transformer's primary winding 13 during each cycle. This occurs because, at this time, the high-voltage capacitor 19 carries a relatively low voltage and the B-field in the transformer does not fully discharge during each cycle. In this regime, the durations of pulses produced by the pulse generator are relatively short. In practice, the successive pulse durations will alternate between two relatively low values, one of which causes the peak current threshold to be exceeded and the other of which does not.

After the voltage on the high-voltage capacitor 19 has risen sufficiently, the apparatus automatically transitions to a second operating regime, in which it is limited by the average current being conducted through the transformer's primary winding 13. In this regime, the durations of the pulses produced by the pulse generator 21 will be increased over those present when operating in the first regime. In this second regime, the successive pulse durations will alternate between two values, one of which causes the average current to exceed the average current threshold and the other of which does not.

After a yet higher voltage on the high-voltage capacitor 19 has been reached, the apparatus automatically transitions to a third operating regime. In this regime, the transformer 11 totally discharges during each cycle, and the pulses produced by the pulse generator 21 have maximum durations.

When the target voltage for the high-voltage capacitor 19 is finally reached, the durations of the pulses produced by the pulse generator 21 will be decremented substantially to zero. This is because no further charging of the capacitor is required, other than to maintain the voltage at its selected high value, e.g., 750 volts.

In all of the operating regimes discussed briefly above, the comparator 101 and resistors 95 and 97 operate continuously to monitor and compare the battery voltage $V_s$ with a predetermined minimum threshold. If the voltage $V_s$ ever drops below the threshold, the successive pulse durations are decremented so as to reduce the current drawn by the transformer's primary winding 13. This delays the charging of the high-voltage capacitor 19, but ensures that other circuitry in the pacemaker reliant on the battery will not be adversely affected.

It should be appreciated from the foregoing description that the present invention provides an improved power converter apparatus for efficiently providing a high-voltage output useful in an implantable defibrillating cardiac pacemaker. The apparatus cyclically pulses a step-up transformer, to controllably charge a high-voltage capacitor, while continuously monitoring several parameters of signals such as peak current, average current, and supply voltage, as well as the output voltage itself. If any of the measured parameters is determined to be outside a predetermined limit, the pulsing of the transformer is incrementally modified. A smooth, efficient charging of the high-voltage capacitor thereby is provided.

Although the invention has been described in detail with reference only to the presently preferred embodiment, those of ordinary skill in the art will appreciate that various modifications can be made without departing from the invention. Accordingly, the invention is defined only by the following claims.

What is claimed is:

1. Power converter apparatus for receiving a relatively low dc input voltage and producing a relatively high dc output voltage, comprising:

a transformer having a primary winding and a secondary winding;

a rectifier connected to the secondary winding of the transformer and including a capacitor that carries the dc output voltage;

a first pulse-width modulator for cyclically applying the input voltage to the primary winding of the transformer, each cyclic application being for a controllably-selected time duration, whereupon an electrical current is induced cyclically in the secondary winding of the transformer, to charge the capacitor of the rectifier; and a feedback controller that measures one or more predetermined parameters of electrical signals present in the transformer and/or rectifier, to produce one or more binary feedback signals sent to the first pulse-width modulator, to controllably adjust the time duration of a subsequent application of the input voltage to the primary winding of the transformer.

2. Power converter apparatus, as defined in claim 1, wherein:

the first pulse-width modulator applies the input voltage to the primary winding of the transformer cyclically at regular intervals of time.

3. Power converter apparatus, as defined in claim 2, wherein:

the feedback control means includes a comparator, operable during each cycle of the first pulse-width modulator, for comparing a predetermined parameter of a signal present in the transformer with a predetermined threshold and for generating a binary control signal according to the outcome of the comparison; and the first pulse-width modulator includes
an up/down counter,
means for cyclically generating a sequence of pulses, each pulse having a time duration selected according to the current count registered in the up/down counter, and
means operable during each cycle for incrementing or decrementing the count registered in the up/down counter according to the binary control signal generated by the comparator.

4. Power converter apparatus, as defined in claim 2, wherein:

the feedback control means includes a comparator, operable during each cycle of the first pulse-width modulator, for comparing a predetermined parameter of a signal present in the transformer with a predetermined threshold and for generating a binary control signal if the threshold is exceeded; and the binary control signal is coupled to the first pulse-width modulator to immediately terminate the current application of the input voltage to the primary winding of the transformer.

5. Power converter apparatus, as defined in claim 1, wherein:
the feedback control means includes a comparator for comparing a measurement of the output voltage with a first predetermined threshold and for generating a first binary feedback signal according to the outcome of the comparison, the first binary feedback signal constituting one of the one or more binary feedback signals.

6. Power converter apparatus, as defined in claim 5, wherein:
the feedback control means further includes
a second pulse-width modulator for intermittently generating a pulse whose duration corresponds to the measurement of the output voltage, and
an optocoupler for coupling the pulses from the second pulse-width modulator to the comparator; and
the comparator includes counter means for measuring the durations of the successively-received pulses and for comparing the measured durations with a first predetermined threshold, to generate the first binary feedback signal.

7. Power converter apparatus, as defined in claim 5, wherein:
the feedback control means further includes
means for measuring the electrical current coupled through the primary coil of the transformer and for generating a second binary feedback signal indicating the relationship between the measured current and a second predetermined threshold, and
means for measuring the total charge coupled through the transformer during each cycle of the first pulse-width modulator and for generating a third binary feedback signal indicating the relationship the measured charge and a third predetermined threshold; and
the first, second and third binary feedback signals are all coupled to the first pulse-width modulator, to controllably adjust the successive time durations of the cyclic applications of the input voltage to the primary winding of the transformer.

8. Power converter apparatus, as defined in claim 7, wherein:
the feedback control means further includes means for measuring the input voltage and for generating a fourth binary feedback signal indicating the relationship between the measured input voltage and a fourth predetermined threshold; and
the fourth binary feedback signal is coupled to the first pulse-width modulator means, to controllably adjust the successive time durations of the cyclic applications of the input voltage to the primary winding of the transformer.

9. Power converter apparatus, as defined in claim 8, wherein:
the feedback control means further includes an OR gate for combining the first, second, third and fourth binary feedback signals, such that the first pulse-width modulator controllably increases the time duration of the next succeeding application of the input voltage to the primary winding of the transformer if all of the first, second, third and fourth feedback signals are in a first binary state and controllably decreases the time duration of the next succeeding application of the input voltage to the primary winding of the transformer if any of the first, second, third and fourth feedback signals is in a second binary state.

10. Power converter apparatus for use in a defibrillating cardiac pacemaker, the apparatus receiving a relatively low dc input voltage and producing a relatively high dc output voltage, the power converter apparatus comprising:
a transformer having a primary winding and a secondary winding;
a rectifier connected to the secondary winding of the transformer and including a capacitor that carries the output voltage;
a first pulse-width modulator for cyclically applying the input voltage to the primary winding of the transformer, at regular intervals of time, each cyclic application being for a controllably-selected time duration, whereupon an electrical current is induced cyclically in the secondary winding of the transformer, to charge the capacitor of the rectifier; and
a feedback controller including
first means for measuring the voltage on the capacitor of the rectifier and for comparing the measured voltage with a first predetermined threshold, to generate a first binary feedback signal according to the outcome of the comparison,
second means for measuring a predetermined parameter of signals present in the transformer, to generate a second binary feedback signal, and
combining means for combining the first and second binary feedback signals to produce a combined binary feedback signal coupled to the first pulse-width modulator, to controllably adjust the time duration of a subsequent application of the input voltage to the primary winding of the transformer.

11. Power converter apparatus, as defined in claim 10, wherein the first pulse-width modulator comprises:
an up/down counter;
means for cyclically generating a sequence of pulses, each pulse having a time duration selected according to the current count registered in the up/down counter; and
means operable during each cycle for incrementing or decrementing the count registered in the up/down counter according to the combined feedback signal produced by the combining means of the feedback controller.

12. Power converter apparatus, as defined in claim 10, wherein:
the feedback controller further includes means for coupling the second binary feedback signal to the first pulse-width modulator, to immediately terminate the current application of the input voltage to the primary winding of the transformer.

13. Power converter apparatus, as defined in claim 11, wherein:
the second means of the feedback controller includes
means for measuring the electrical current coupled through the primary coil of the transformer and for generating the second binary feedback signal indicating the relationship between the measured current and a second predetermined threshold,
means for measuring the total charge coupled through the transformer during each cycle of the first pulse-width modulator and for generating a third binary feedback signal indicating the relationship between the measured charge and a third predetermined threshold, and
means for measuring the input voltage and for generating a fourth binary feedback signal indicating the relationship between the measured voltage and a fourth predetermined threshold; and the combining means of the feedback controller includes an OR gate for ORing together the first, second, third and fourth binary feedback signals to produce the combined feedback signal, the combined feedback signal being in a first binary state, to controllably increase the time duration of the next succeeding application of the input voltage to the primary winding of the transformer, if all of the first, second, third and fourth feedback signals are in a first binary state, and the combined feedback signal being in a second binary state, to controllably decrease the time duration of the next succeeding application of the input voltage to the primary winding of the transformer, if any of the first, second, third and fourth feedback signals is in a second binary state.

14. Power converter apparatus for receiving a relatively low dc input voltage and producing a relatively high dc output voltage, comprising:

a transformer having a primary winding and a secondary winding;

a rectifier connected to the secondary winding of the transformer and including a capacitor that carries the output voltage;

a first pulse-width modulator for periodically applying the input voltage to the primary winding of the transformer, each periodic application being for a controllably-selected time duration, whereupon an electrical current is induced periodically in the secondary winding of the transformer, to charge the capacitor of the rectifier; and feedback control means operable in a first regime to condition the first pulse-width modulator to apply input power periodically to the primary winding of the transformer for time durations selected to provide a predetermined peak electrical current through the primary winding, and further operable in a second regime to condition the first pulse-width modulator to apply input power periodically to the primary winding for time durations selected to provide a predetermined average electrical current through the primary winding.

15. Power converter apparatus, as defined in claim 14, wherein:

the first pulse-width modulator includes
an up/down counter, and
means for cyclically generating a sequence of pulses, each pulse having a time duration selected according to the current count registered in the up/down counter; and the feedback control means operates during each cycle to increment or decrement the count registered in the up/down counter.

16. Power converter apparatus, as defined in claim 14, wherein:

the feedback control means includes a comparator for comparing a measurement of the output voltage with a first predetermined threshold, to generate a first binary feedback signal according to the outcome of the comparison, the first binary feedback signal being coupled to the first pulse-width modulator, to controllably adjust the successive time durations of the periodic applications of the input voltage to the primary winding of the transformer.

17. Power converter apparatus, as defined in claim 16, wherein:

the feedback control means further includes
a second pulse-width modulator for periodically generating a pulse whose duration corresponds to the measurement of output voltage, and
an optocoupler for coupling the pulses from the second pulse-width modulator to the comparator; and the comparator includes counter means for measuring the durations of the successively-received pulses and for comparing the measured durations with a first predetermined threshold, to generate the first binary feedback signal.

18. Power converter apparatus, as defined in claim 16, wherein:

the feedback control means further includes
means for measuring the electrical current coupled through the primary coil of the transformer and for generating a second binary feedback signal indicating the relationship between the measured current and a second predetermined threshold, and
means for measuring the total charge coupled through the transformer during each cycle of the first pulse-width modulator and for generating a third binary feedback signal indicating the relationship the measured charge and a third predetermined threshold; and the first, second and third binary feedback signals are all coupled to the first pulse-width modulator, to controllably adjust the successive time durations of the cyclic applications of the input voltage to the primary winding of the transformer.

19. Power converter apparatus, as defined in claim 18, wherein:

the feedback control means further includes means for measuring the input voltage and for generating a fourth binary feedback signal indicating the relationship between the measured input voltage and a fourth predetermined threshold; and the fourth binary feedback signal is coupled to the first pulse-width modulator means, to controllably adjust the successive time durations of the cyclic applications of the input voltage to the primary winding of the transformer.

20. Power converter apparatus, as defined in claim 19, wherein:

the feedback control means further includes an OR gate for ORing together the first, second, third and fourth binary feedback signals, such that the first pulse-width modulator controllably increases the time duration of the next succeeding application of the input voltage to the primary winding of the transformer if all of the first, second, third and fourth feedback signals are in a first binary state and controllably decreases the time duration of the next succeeding application of the input voltage to the primary winding of the transformer if any of the first, second, third and fourth feedback signals is in a second binary state.

* * * * *